United States Patent [19]

Mastroianni et al.

[11] 4,308,303
[45] Dec. 29, 1981

[54] FLOCKED, FOAM-COATED, FIBROUS-REINFORCED, WATER VAPOR PERMEABLE, BACTERIAL BARRIER

[75] Inventors: Michael J. Mastroianni, Spotswood; Joseph T. Lin, Kendall Park, both of N.J.

[73] Assignee: Johnson & Johnson, New Brunswick, N.J.

[21] Appl. No.: 177,702

[22] Filed: Aug. 12, 1980

Related U.S. Application Data

[63] Continuation-in-part of Ser. No. 956,838, Nov. 2, 1978, abandoned.

[51] Int. Cl.³ .............................................. A61F 13/00
[52] U.S. Cl. ..................................... 428/90; 428/286; 428/287; 428/288; 428/296; 428/907; 428/315.9; 428/316.6
[58] Field of Search ................... 428/86, 90, 286, 287, 428/288, 296, 304, 305, 310, 311, 315, 907; 128/132 D, 155, 156

[56] References Cited

U.S. PATENT DOCUMENTS

| | | | |
|---|---|---|---|
| 3,745,057 | 7/1973 | Loft | 428/44 |
| 3,870,593 | 3/1975 | Elton | 128/132 D |
| 3,949,742 | 4/1976 | Nawakowski | 428/315 |
| 3,985,130 | 10/1976 | Wideman | 128/132 D |
| 4,056,646 | 11/1977 | Westfall | 428/315 |

Primary Examiner—Marion McCamish
Attorney, Agent, or Firm—Charles J. Metz

[57] ABSTRACT

A flocked, foam-coated, fibrous-reinforced, water vapor permeable, bacterial barrier having the appearance of fabric, and being capable of filtering bacteria is disclosed. The barrier comprises a microporous polyolefin film coated on at least one surface with a foamed latex polymer, flocked fibers on the exterior surface of said foamed latex polymer, and a web of spunbonded fibers on the exterior surface of the flocked, foamed latex polymer.

16 Claims, No Drawings

FLOCKED, FOAM-COATED, FIBROUS-REINFORCED, WATER VAPOR PERMEABLE, BACTERIAL BARRIER

This application is a continuation-in-part of Ser. No. 956,838, filed Nov. 2, 1978, now abandoned.

The invention relates to a flocked, foam-coated, fibrous-reinforced, water vapor permeable, bacterial barrier.

BACKGROUND OF THE INVENTION

This is a need for bacterial barriers that are also water vapor permeable, from which surgical drapes and gowns and similar articles can be fabricated. The desired properties of such barriers would include:
1. Ability to prevent passage of bacteria, even under moderate pressure such as would be encountered by a surgeon leaning against a sharp edge or corner;
2. Comfortable to wear, which requires a certain minimum moisture vapor transmission rate. Of secondary importance is the amount of skin contact;
3. Sterilizability;
4. Absence of linting;
5. Low cost so that the article can be used once and then discarded (to eliminate the need for the hospital to launder and sterilize the article);
6. Appropriate aesthetics, including a fabric-like appearance. This is especially important for surgical gown material; and
7. Sufficient strength to withstand (a) fabrication into finished products, (b) normal handling, and (c) the stresses and strains incurred in use.

The present invention is directed to the provision of a bacterial barrier that has the above-enumerated properties. As far as is known, no earlier material has all of these properties.

BROAD STATEMENT OF THE INVENTION

The invention provides a water vapor permeable bacterial barrier having the appearance of fabric, and being capable of filtering bacteria. The barrier comprises a microporous plastic film, said film being coated on at least one side thereof with a foamed latex polymer having flocked fibers on its exterior surface, with a web of spunbonded fibers on the surface of the flocked, foamed latex polymer.

THE PRIOR ART

The use of microporous films per se as bacterial barriers has been disclosed. For instance, see Loft et al., U.S. Pat. No. 3,745,057.

The use of microporous films in fabricating medical dressings, surgical drapes, etc., has been disclosed. For instance, see Strauss, U.S. Pat. No. 3,214,501, Bierenbaum et al., U.S. Pat. No. 3,426,754, and Elton et al., U.S. Pat. No. 3,870,593.

Various composites containing foamed latex polymer and flocked fibers have been disclosed by Klein, U.S. Pat. Nos. 3,961,116 and 3,903,331, and Westfall et al., U.S. Pat. No. 4,056,646.

The use of certain flocked fabrics in the fabrication of hospital drapes and surgical gowns is disclosed by Palmer et al. in U.S. Pat. No. 3,956,553.

Composites of a polyurethane ionomer latex foam coated on a textile fabric are disclosed by Bocks et al. in U.S. Pat. No. 4,029,534.

A surgical drape composed of a nonporous plastic film, nonwoven fabric, and latex adhesive is disclosed by Hansen in U.S. Pat. No. 3,809,077.

A burn dressing composed of a permeable elastomeric film having bonded thereto a fabric made of a fiber that is absorbable by living tissue, is disclosed by Augurt in U.S. Pat. No. 3,903,882.

The artificial leather art contains many disclosures of porous polymeric coatings combined with fibrous materials.

Outdoor garments (e.g., parkas) made from "Gore-Tex" (a microporous polytetrafluoroethylene film) sandwiched between nylon taffeta and nylon tricot, are sold commercially (see page 21 L. L. Bean's Spring 1978 catalogue).

DETAILED DESCRIPTION OF THE INVENTION

The invention employs microporous plastic films which are capable of filtering bacteria, but which are sufficiently water vapor permeable to be comfortable to wear. By "capable of filtering bacteria" is meant that water that has been inoculated with bacteria can be forced through the film under moderate pressure (e.g., about 5–20 psi), with sterile water being recovered on the other side of the film. The requisite filtering capabilities are ordinarily achieved when the maximum pore size is about 0.2 micron, as determined by the bubble point method using isopropyl alcohol as the wetting liquid. The bubble point method for pore size determination is the procedure of ASTM F316-70.

The water vapor permeability requirements for comfort cannot be stated with exact precision because conditions of end-use vary widely. When the body is at rest, normal skin exudes moisture at a rate of the order of 60 grams per 100 square inches per 24 hours. Thus, adding a factor for perspiration, the minimum moisture vapor transmission rate (MVTR) required for comfort is about 100, and preferably about 250, grams per 100 square inches per 24 hours. (MVTR is measured by ASTM E96-66, Procedure E.) Of course, the higher the MVTR value is, the more comfortable the barrier will be.

The preferred plastics from which to produce the microporous film are olefin polymers such as film grade isotactic polypropylene and film grade high density polyethylene. Polypropylene having a melt flow rate (by ASTM D-1238, Method L, $I_2$ at 230° C.) of from about 0.5 to about 8 grams per 10 minutes, and high density polyethylene having a melt index (by ASTM D-1238-65, Method E, $I_2$ at 190° C.) of from about 0.05 to about 1, are generally suitable.

The preferred olefin polymer microporous films, and microporous films made from other stretch orientable plastics such as thermoplastic polyurethane, used in the invention can be made by stretching a film containing minute fracture sites or pore-nucleating agents such as finely divided filler and/or minute crystalline domains. The use of a finely divided, inorganic, water-insoluble, inert filler such as calcium carbonate having an average particle size of less than 3 microns is preferred. It is generally preferred to use a filler that has been surface treated to impart hydrophobic (or oleophilic) properties in order to facilitate dispersion and mixing with the olefin polymer. As a general rule, the filler is employed in amounts of from about 40 to about 70 weight per cent, based on weight of total polymer plus filler. At proportions below about 40 weight per cent, porosity tends to become insufficient, and at proportions above about 70 weight per cent, the strength properties of the film tend to be adversely affected (in particular, the film becomes brittle). The above-stated proportions reflect experience with calcium carbonate having an average particle size of about 3 microns. The practical range of proportions may differ somewhat with fillers whose specific gravities differ significantly from calcium carbonate, and with fillers having significantly different particle sizes. For instance, it is anticipated that less filler can be used, perhaps as little as about 20 weight per cent, while still achieving the desired porosity, if it has much smaller particle size, e.g., an average of 0.1 micron or less.

It is desirable in many cases to employ a small proportion of a polymeric modifier in an olefin polymer film in order to improve the tear resistance, impact strength, and the aesthetic properties (hand, drape, etc.) of the film. The polymeric modifier also serves to facilitate dispersion of the filler in the olefin polymer.

Such polymeric modifiers include ethylene-propylene rubbers, ethylene-vinyl acetate copolymers, ethylene-acrylic ester (e.g., ethyl acrylate) copolymers, polybutene, thermoplastic polyurethane, and thermoplastic rubbers. The thermoplastic rubbers are preferred.

The polymeric modifier is ordinarily employed in proportions of up to about 10–15 weight per cent, based on total weight of the film. The maximum amount of polymeric modifier that can be employed is that amount which substantially impairs the orientability, and hence ability to form pores, of the film. This maximum amount will vary somewhat from one formulation to another, and can readily be determined by routine experimentation.

The thermoplastic rubbers, which are the preferred polymeric modifiers, are block copolymers of styrene and butadiene or isoprene. They constitute a known class of materials, which is described in an article by S. L. Aggarwal, entitled "Structure And Properties Of Block Polymers And Multi-Phase Polymer Systems: An Overview Of Present Status And Future Potential", in *Polymer*, Volume 17, November 1976, pages 938–956.

It is desirable to thoroughly mix the polymer(s) and filler prior to film formation. A twin screw extruder/pelletizer has been found to be very useful for this purpose.

Films based on the above-described formulations are made by known methods. Illustrations include tubular blown film methods and cast film (i.e., slot die extrusion) methods.

The film is made microporous by stretching. The film is preferably stretched as much as possible in both machine and cross directions, in order to achieve maximum porosity. As a practical matter, however, highly filled films cannot be stretched beyond a certain point that is dependent, in part, upon factors such as nature and proportion of polymer(s) and filler, gauge or thickness of the unstretched film, method of making the film (e.g., case, tubular blown, etc.) and stretching temperature. To illustrate, 5-mil cast polypropylene or high density polyethylene film containing about 50 per cent filler can be hot stretched about 3× in both directions to produce a 1-mil microporous film. Tubular blown polypropylene or high density polyethylene film having a gauge of from 1.5 to 2.5 mils can be stretched in the machine direction at room temperature about 3× to produce about 1 to 1.5 mil microporous film.

Film produced as described above, containing about 50 weight per cent filler having an average particle size of about 3 microns, will usually have a maximum pore size not greater than about 0.2 micron and a moisture vapor transmission rate of about 100 to 150 grams per 100 square inches per 24 hours.

Microporous plastic films made by other processes can also be employed. Such other processes include the technique of preparing a plastic film containing a finely divided, soluble filler, and leaching out the filler with a solvent. This method is less preferred because it is generally more expensive than the stretching process described above in detail.

In one desirable aspect of the invention, the microporous film is produced from two layers of film. In this aspect, two separate films (or an unslit tubular blown film) are superimposed on one another and are then fed through hot rolls maintained near the melting point of the film to form a laminate that cannot be pulled apart without destroying the films. (In effect, the two layers of film are heat sealed to each other.) The laminate is then stretched as taught above to form a microporous film. The advantage of using the double layer construction is that the probability of having pin holes or other defects that extend all the way through the film is greatly reduced. Gel specs, impurities, or other foreign materials that might cause such defects would be found in only half the thickness of the double layer film product, thereby substantially reducing the probability of pin hole formation from these causes.

The desirable effects of a double layer film may also be produced by coextrusion wherein two separate streams of polymer melt are joined in laminar flow just upstream of the die. By so doing, gel specs, etc., would be isolated in half the extruded film thickness, thereby reducing the probability of pin hole formation.

The microporous film described above is coated with a foamed latex polymer on at least one side, and flocked fibers are applied to the external surface of the foam. The latex polymers employed are known materials. They are generally film-forming grade materials, including aqueous-based acrylic latexes, styrene-butadiene latexes, polyvinyl acetate latexes, natural or synthetic rubber latexes, and any other aqueous-based latex made from a water-insoluble polymer. The acrylic latexes are preferred.

The foaming of the latex is effected by beating air into the latex so that the volume of the latex is increased from about 2 to about 18 times its original volume. (The latex employed will ordinarily contain conventional additives such as surfactants, foam stabilizers, thickeners, cross-linking agents, colorants and/or opacifying agents, and the like, empoyed in the usual amounts.)

The foamed latex is then applied to the surface of the microporous plastic film by knife coating, reverse roll coating, or other conventional procedure. Flocked fibers are then applied to the external surface of the foam by spraying, dusting, sieving, or the like. The flock is preferably applied only in the amount required to coat the latex. This minimizes linting. Short cut cotton flock is preferred, although other types of flock can be used. The flocked and foamed film is then dried to remove the water from the foamed latex, as by passing through a heated tunnel maintained at a temperature of about 80° C. to about 150° C. for a period of about 5 to about 90 seconds. If desired, the foamed and flocked film can be passed through a pair of rolls under moderate pressure to crush the foam. This can be done either before or after curing. Loose flock, if any, is then removed by vacuum, brushing, beater bars, or a combination thereof. The flock is an important contributor to the textile-like appearance of the bacterial barrier of the invention.

If desired, a coating of foamed latex polymer and flocked fibers can be applied to the other surface of the microporous film. This will usually be done before the crushing and final drying or curing steps. The final drying and curing step is carried out by subjecting the latex polymer to a temperature within the range of from about 80° C. to about 150° C. for a period of from about 10 to 90 seconds. The temperatures in both the initial drying step and final drying and curing step are selected to avoid excessive shrinking of the microporous film. Thus, temperatures used for high density polyethylene microporous film are usually lower than those used for polypropylene microporous film.

Prior to the final drying and curing step, a web of spunbonded fibers is placed on top of the flocked latex polymer foam, and is bonded to the latex polymer by the application of moderate heat and pressure. For instance, a temperature of from about 90° to about 150° C. and a pressure of from about ½ to about 30 psi can be applied for a period of a few seconds up to about a minute. This can be done by passing the composite through a pair of hot, embossed nip rolls under moderate pressure (e.g., from about 1 to about 10 pounds per linear inch.)

Nylon spunbonded webs are preferred, although other spunbonded webs (e.g., polyester and polypropylene) can also be used.

The principal advantage obtained in employing the spunbonded web on the exterior surface of the flocked latex polymer foam is the minimization of linting. Certain mechanical properties such as tear strength are also improved.

The exact weights and proportions of the components of the fibrous-reinforced, water vapor permeable, bacterial barrier of the invention have not been found to be narrowly critical. Typical preferred weights are the following:

|  | Ounces per square yard |
|---|---|
| Microporous film (0.5 to 1.5 mils) | ¼ to 1 |
| Latex polymer foam (per side) | 0.2 to 0.5 |
| Flocking, 0.3-0.4 mm, cotton (per side) | 0.1 to 0.4 |
| Spunbonded fibrous reinforcing web (per side) | 0.2 to 0.6 |

The bacterial barrier of the invention is composed mostly of plastic. That is, in most cases, the weight of the microporous film plus the latex polymer foam, will equal or exceed the weight of the fiber flocking plus the fibrous reinforcing web. Nevertheless, especially when the microporous film is coated on both surfaces with the flocked foam, the bacterial barrier of the invention resembles fabric in appearance more than plastic. By this is meant that the bacterial barrier has visual appearance, hand, and drape properties that are characteristic of fabric, and the flocked foam surfaces do not have the shiny visual appearance and the plastic feel that is characteristic of polyolefin films.

The bacterial barrier of the invention exhibits sufficient strength to withstand fabrication into finished products, normal handling, and use. The dimensional stability, tear strength, puncture and burst resistance, and tensile strength, are all adequate for the intended purpose, despite the light weight of the material. Thus, it can be seen that the bacterial barrier of the invention combines a number of normally contradictory properties: water vapor permeable, yet also a bacterial barrier; composed largely of plastic, yet has the appearance of fabric; light in weight and low cost, yet strength adequate for its intended purpose; contains fiber flocking, yet is substantially lint-free.

The following Examples illustrate the production of the bacterial barriers of the invention:

EXAMPLE 1

Film Preparation

The following components are mixed in a Werner & Pfleiderer pelletizer:

|  | Parts, by weight |
|---|---|
| Polypropylene[1] | 45 |
| Thermoplastic Rubber[2] | 5 |
| Calcium Carbonate[3] | 50 |

[1] Hercules "Pro-Fax" 6723; melt flow of 0.8; heat stabilized
[2] "Solprene" 418, a radial block copolymer; 85/15 (by weight) isoprene/styrene ratio
[3] "Hi-pflex-100"; average particle size 3 microns; with a hydrophobic surface treatment The pelletizer is a twin screw, three start profile, extruder (screw diameter—53 millimeters; L/D=35). The materials are metered at the back end of the screw, and are extruded into several strands, which are chopped to form pellets. The extruder barrel temperature varies from about 345° to about 410° F.

Blown tubular film is produced from the above-described pellets using a 1 inch, 24/1 (L/D), single screw extruder having a 20-mil gauge, 2-½ inch diameter die. The screen pack behind the die contains 40/60/40 mesh screens; the back pressure is 2000 to 3500 psi, the screw speed is 50 to 80 RPM, the extruder temperature is 410° to 440° F., and the die temperature is 450° F. The blow up ratio is 1.3 to 2.8, the gauge of the film is 1.5 to 2.5 mils, and the lay flat width of the film is 5 to 11 inches.

Film Stretching

The film is longitudinally stretched 3× at room temperature using two sets of 4-roll godets. Typical godet speeds are 0.8 feet per minute for the first set and 2.4 feet per minute for the second. For starting gauges of 1.5 to 2.5 mils, typical finished gauges are 1 to 1.5 mils, with a 10 to 20 percent width reduction. The film has a maximum pore size (by the bubble point method, using isopropyl alcohol as the wetting liquid) of 0.2 micron, and a moisture vapor transmission of about 100 grams per 100 square inches per 24 hours.

Foam Coating

The following formulation is prepared by adding the ingredients in the order listed:

|  | Parts, dry weight | Parts, total weight |
|---|---|---|
| Water | — | 26.69 |
| Hydroxyethyl-cellulose | 0.09 | 0.09 |
| Acrylic latex | 34.23 | 60.27 |
| Ammonia, to pH = 7 |  |  |

-continued

|  | Parts, dry weight | Parts, total weight |
|---|---|---|
| Polyethylene glycol di-2-octoate | 4.74 | 4.74 |
| Ammonium Stearate | 1.55 | 1.55 |
| Sodium lauryl sulfate | 0.14 | 0.47 |
| Ammonia, to pH 9.5 |  |  |

(4)"Cellosize" HEC QP 4400 H; viscosity is 4400 cps in 2% aqueous solution
(5)"UCAR" 872 - Ethyl acrylate/2-ethylhexyl acrylate/N-methylol -acrylamide/acrylic acid
(6)"Flexol" 4GO
(7)"Paranol" F-7859 (aqueous solution)

The foregoing formulation is foamed by beating with 8 volumes of air. The foam is applied to the above-described microporous film by knife coating a 5-10 mil thick wet layer. Cotton flock (0.3-0.4 mil) is dusted on the surface of the foam using a vibrating sieve. (The sieve has 900 0.5 mm openings per square inch.) The flocked, foam-coated film is subjected to a temperature of 200° F. for about 1 minute, and the excess flock is removed by vacuuming and brushing. The coating, flocking, drying, and cleaning process is repeated on the other side.

A light weight (0.4 ounce per square yard) nylon spunbonded web is placed against one surface of the above-described product, and the composite is pressed under moderate pressure (about 10 psi) at 225° F. for 30 seconds.

The product is a water vapor permeable bacterial barrier capable of filtering bacteria.

We claim:

1. A fibrous reinforced, water vapor permeable, bacterial barrier having the appearance of fabric, and being capable of filtering bacteria, comprising a microporous plastic film, said film being both water vapor permeable and capable of filtering bacteria, said microporous film being coated on at least one surface thereof with a foamed latex polymer, flocked fibers on the exterior surface of said foamed latex polymer, and a spunbonded fibrous web bonded to the same exterior surface of said foamed latex polymer.

2. The fibrous reinforced, water vapor permeable, bacterial barrier of claim 1 wherein the spunbonded fibrous web is composed of nylon, polyester, or polypropylene fibers.

3. The fibrous reinforced, water vapor permeable, bacterial barrier of claim 1 wherein the spunbonded web is a nylon spunbonded web having a weight of from about 0.2 to about 0.6 ounce per square yard.

4. The bacterial barrier of claim 1, 2, or 3, wherein the foamed latex polymer is a foamed acrylic polymer.

5. The water vapor permeable bacterial barrier of claim 4 wherein the microporous film weighs from about ¼ to about 1 ounce per square yard, wherein the foamed latex polymer weighs from about 0.2 to about 0.5 ounce per square yard side, and wherein the flocking weighs from about 0.1 to about 0.4 ounce per square yard per side.

6. The bacterial barrier of claim 5 wherein the plastic is an olefin polymer.

7. The bacterial barrier of claim 4 wherein the plastic is an olefin polymer.

8. The bacterial barrier of claim 1, 2, or 3 wherein the plastic is an olefin polymer.

9. A fibrous reinforced, water vapor permeable, bacterial barrier capable of filtering bacteria, comprising a microporous plastic film, said film being both water vapor permeable and capable of filtering bacteria, said microporous film being coated on at least one surface thereof with a foamed latex polymer, flocked fibers on the exterior surface of said foamed latex polymer, and a spunbonded fibrous web bonded to the same exterior surface of said foamed latex polymer.

10. The fibrous reinforced, water vapor permeable, bacterial barrier of claim 9 wherein the spunbonded fibrous web is composed of nylon, polyester, or polypropylene fibers.

11. The fibrous reinforced, water vapor permeable, bacterial barrier of claim 9 wherein the spunbonded web is a nylon spunbonded web having a weight of from about 0.2 to about 0.6 ounce per square yard.

12. The bacterial barrier of claim 9, 10, or 11, wherein the foamed latex polymer is a foamed acrylic polymer.

13. The water vapor permeable bacterial barrier of claim 12 wherein the microporous film weighs from about ¼ to about 1 ounce per square yard, wherein the foamed latex polymer weighs from about 0.2 to about 0.5 ounce per square yard side, and wherein the flocking weighs from about 0.1 to about 0.4 ounce per square yard per side.

14. The bacterial barrier of claim 13 wherein the plastic is an olefin polymer.

15. The bacterial barrier of claim 12 wherein the plastic is an olefin polymer.

16. The bacterial barrier of claim 9, 10, or 11 wherein the plastic is an olefin polymer.

* * * * *